United States Patent [19]

Borzatta et al.

[11] Patent Number: 5,091,450
[45] Date of Patent: Feb. 25, 1992

[54] PIPERIDINE-TRIAZINE COMPOUNDS CONTAINING TETRAHYDROFURAN OR TETRAHYDROPYRAN GROUPS, FOR USE AS STABILIZERS FOR ORGANIC MATERIALS

[75] Inventors: Valerio Borzatta; Graziano Vignali, both of Bologna, Italy

[73] Assignee: Ciba-Geigy Corporation, Ardsley, N.Y.

[21] Appl. No.: 733,483

[22] Filed: Jul. 22, 1991

[30] Foreign Application Priority Data

Jul. 27, 1990 [IT] Italy .................. 21092 A/90

[51] Int. Cl.⁵ .................. C08K 5/3492; C07D 295/00; C07D 251/68
[52] U.S. Cl. .................. 524/100; 106/176; 252/47.5; 252/51.5 R; 260/398.5; 540/575; 544/113; 544/198; 544/209; 544/212
[58] Field of Search .................. 524/100; 544/198, 209, 544/212, 113; 540/575; 260/398.5; 106/176; 252/47.5, 51.5 R

[56] References Cited

U.S. PATENT DOCUMENTS

| | | | |
|---|---|---|---|
| 4,086,204 | 4/1978 | Cassandrini et al. | 544/207 |
| 4,263,434 | 4/1981 | Cassandrini et al. | 544/212 |
| 4,315,859 | 2/1982 | Nikles | 544/198 |
| 4,331,586 | 5/1982 | Hardy | 544/113 |
| 4,335,242 | 6/1982 | Wiezer et al. | 544/198 |
| 4,459,395 | 7/1984 | Cantatore | 544/198 |
| 4,477,615 | 10/1984 | Raspanti et al. | 544/198 |
| 4,547,548 | 10/1985 | Cantatore . | |

FOREIGN PATENT DOCUMENTS

| | | |
|---|---|---|
| 0053775 | 6/1982 | European Pat. Off. . |
| 117229 | 8/1984 | European Pat. Off. . |
| 299925 | 1/1989 | European Pat. Off. . |
| 0365469 | 4/1990 | European Pat. Off. . |
| 376886 | 7/1990 | European Pat. Off. . |
| 63-196654 | 8/1988 | Japan . |

Primary Examiner—Veronica P. Hoke
Attorney, Agent, or Firm—Luther A. R. Hall

[57] ABSTRACT

Compounds of the formula (I)

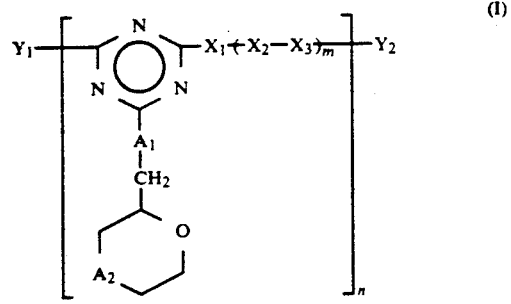

in which $A_1$ is e.g. —O— or >N—$R_1$ where $R_1$ is e.g. hydrogen, methyl, 2,2,6,6-tetramethyl-4-piperidyl or 1,2,2,6,6-pentamethyl-4-piperidyl, $A_2$ is e.g. a direct bond or —$CH_2$—, $X_1$ and $X_3$ which can be identical or different are e.g. a group of the formula (IIIa) or (IIIb)

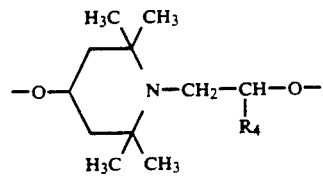

in which $A_3$ and $A_4$ which can be identical or different are e.g. an >N—$R_1$ group where $R_1$ is as defined above, $R_3$ is e.g. —$(CH_2)_{2-6}$— or —$(CH_2)_3$—O—$(CH_2)_2$-4—O—$(CH_2)_3$— and $R_4$ is e.g. hydrogen or methyl, $X_2$ is e.g. 2-hydroxytrimethylene or a group of the formula (IVa)

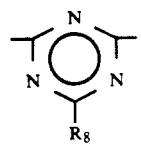

where $R_8$ is e.g. a group of the formula (V)

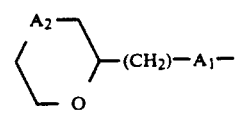

m is e.g. zero or 1, n is e.g. a number from 1 to 10, $Y_1$ is e.g. OH, ONa, OK, a group $R_8$ or a group —$X_1Z$ or —$X_3Z$ with Z being e.g. hydrogen or methyl and $Y_2$ is e.g. hydrogen, methyl or a group

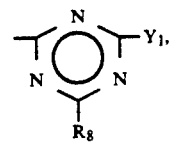

with the provisos that (1) $X_1$ or $X_2$ or $X_3$ contains a group of the formula (II), (Abstract continued on next page.)

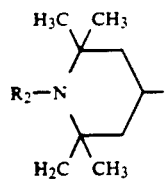
(II)
with $R_2$ being e.g. hydrogen or methyl, that (2) each of the groups $A_1$, $A_2$, $X_1$, $X_2$, $X_3$ and m has the same or a different definition in the individual recurring structural units of the formula (I) and that (3) the only definition of $Y_1$ is the group $-X_1Z$, when m is zero and n is 1.
12 Claims, No Drawings

PIPERIDINE-TRIAZINE COMPOUNDS CONTAINING TETRAHYDROFURAN OR TETRAHYDROPYRAN GROUPS, FOR USE AS STABILIZERS FOR ORGANIC MATERIALS

The present invention relates to novel piperidine-triazine compounds, to their use a light stabilizers, heat stabilizers and oxidation stabilizers for organic materials, in particular synthetic polymers, and to organic materials thus stabilized.

It is known that synthetic polymers undergo a progressive deterioration of the physical properties, such as loss of mechanical resistance and colour changes when they are exposed to the action of sunlight or other sources of ultraviolet light in the presence of oxygen.

To retard the deleterious effect of ultraviolet radiation on synthetic polymers, additives having light-stabilizing properties are used, such as some derivatives of benzophenone and benzotriazole, nickel complexes, alkylidenemalonates, cyanoacrylates, aromatic oxamides or sterically hindered amines.

Some triazine oligomers containing 2,2,6,6-tetramethyl-piperidine groups and their use as stabilizers for synthetic polymers have been reported in U.S. Pat. Nos. 4,086,204, 4,315,859, 4,331,586, 4,335,242, 4,459,395, 4,477,615 and 4,547,548, in European Laid Open Print 117,229 and in Japanese Laid Open Print Sho 63-196,654.

Moreover, piperidine-triazine compounds containing the tetrahydrofurfurylamino group and their use as stabilizers for synthetic polymers are described in European Laid Open Print 365,469.

The present invention relates to novel piperidine-triazine compounds of the formula (I)

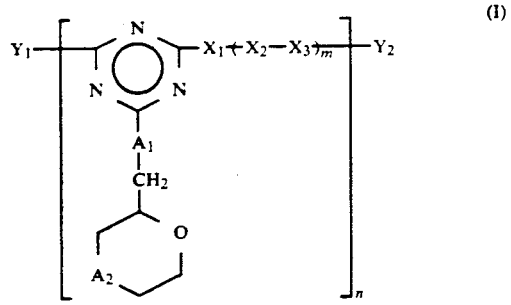

in which $A_1$ is —O— or >N—$R_1$, in which $R_1$ is hydrogen, $C_1$-$C_{18}$alkyl, $C_5$-$C_{12}$cycloalkyl which is unsubstituted or mono-, di- or tri-substituted by $C_1$-$C_4$alkyl; $C_7$-$C_9$phenylalkyl which is unsubstituted or mono-, di- or tri-substituted on the phenyl by $C_1$-$C_4$alkyl; tetrahydrofurfuryl or a group of the formula (II)

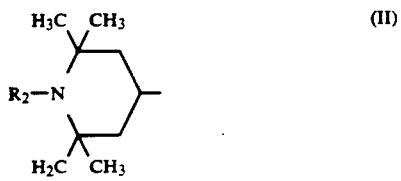

in which $R_2$ is hydrogen, $C_1$-$C_8$alkyl, O•, OH, NO, $CH_2CN$, $C_1$-$C_{18}$alkoxy, $C_5$-$C_{12}$cyclo-alkoxy, $C_3$-$C_6$alkenyl, $C_7$-$C_9$phenylalkyl which is unsubstituted or mono-, di- or tri-substituted on the phenyl by $C_1$-$C_4$alkyl; or $R_2$ is $C_1$-$C_8$acyl, $A_2$ is a direct bond or —$CH_2$—, $X_1$ and $X_3$ which can be identical or different are one of the groups of the formulae (IIIa)–(IIIe)

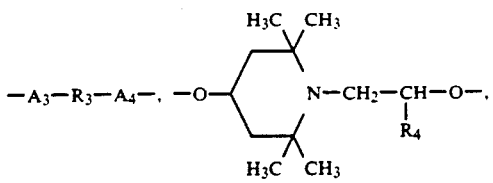

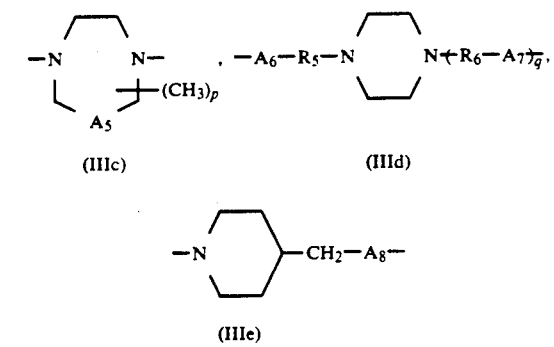

in which $A_3$, $A_4$, $A_6$, $A_7$ and $A_8$ which can be identical or different are as defined for $A_1$, $R_3$ is $C_2$-$C_{12}$alkylene, $C_4$-$C_{12}$alkylene interrupted by 1, 2 or 3 oxygen atoms or by 1 or 2 >N—$R_7$ groups, where $R_7$ is as defined for $R_1$ or is $C_1$-$C_8$acyl or ($C_1$-$C_8$alkoxy)-carbonyl; or $C_5$-$C_7$cycloalkylene, $C_5$-$C_7$cycloalkylene-di-($C_1$-$C_4$alkylene), $C_1$-$C_4$alkylene-di-($C_5$-$C_7$cycloalkylene), $C_2$-$C_4$alkylidene-di-($C_5$-$C_7$cycloalkylene), phenylene, phenylene-di-($C_1$-$C_4$alkylene), $C_1$-$C_4$alkylenediphenylene or $C_2$-$C_4$alkylidenediphenylene, it being possible for each phenylene group to be unsubstituted or mono- or di-substituted by $C_1$-$C_4$alkyl, $R_4$ is hydrogen, $C_1$-$C_8$alkyl or phenyl, $A_5$ is a direct bond or —$CH_2$—, p is zero, 1, 2 or 3, $R_5$ and $R_6$ which can be identical or different are $C_2$-$C_6$alkylene and q is zero or 1, $X_2$ is $C_2$-$C_{12}$alkylene, $C_4$-$C_{12}$alkylene interrupted by 1, 2 or 3 oxygen atoms; 2-hydroxytrimethylene, xylylene, carbonyl or one of the groups of the formulae (IVa)–(IVe)

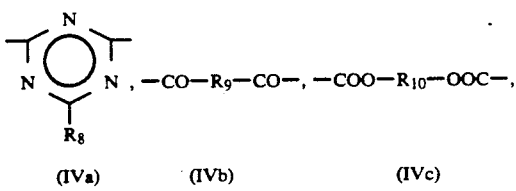

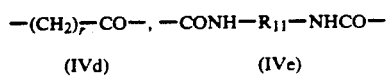

in which $R_8$ is a group of the formula (V)

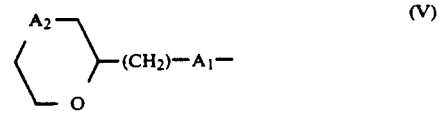

with $A_1$ and $A_2$ as defined above, or $R_8$ is a group —$OR_{12}$, —$SR_{12}$ or

in which $R_{12}$, $R_{13}$ and $R_{14}$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl; $C_3$-$C_{18}$alkenyl, phenyl which is unsubstituted or mono-, di- or tri-substituted by $C_1$-$C_4$alkyl or $C_1$-$C_4$alkoxy; $C_7$-$C_9$phenylalkyl which is unsubstituted or mono-, di- or tri-substituted on the phenyl by $C_1$-$C_4$alkyl; a group of the formula (II), $C_2$-$C_4$alkyl substituted in the 2-, 3- or 4-position by $C_1$-$C_8$alkoxy or by di-($C_1$-$C_4$alkyl)-amino; or the group

is a 5-membered to 7-membered heterocyclic group, $R_9$ is a direct bond, $C_1$-$C_{12}$alkylene, cyclohexylene, methylcyclohexylene or phenylene, $R_{10}$ is as defined for $R_3$, r is an integer from 1 to 10 and $R_{11}$ is as defined for $R_3$ or a group

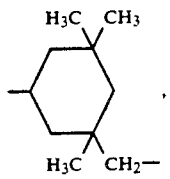

m is zero, 1, 2, 3 or 4, n is a number from 1 to 50, $Y_1$ is Cl, OH, ONa, OK, a group $R_8$ or a group $-X_1Z$ or $-X_3Z$ where Z is hydrogen, methyl, benzyl, $C_1$-$C_8$alkcyl or ($C_1$-$C_8$alkoxy)-carbonyl and $Y_2$ is Z, a group

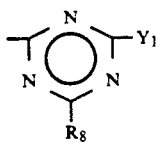

or a group $-X_2OH$; the provisos applying to the compounds of the formula (I) that (1) $X_1$ or $X_2$ or $X_3$ contains a group of the formula (II) and that (2) in the individual recurring structural units of the formula (I), each of the groups $A_1$, $A_2$, $X_1$, $X_2$, $X_3$ and m has the same or a different definition and that (3I), when m is zero and n is 1, the only definition of $Y_1$ is the group $-X_1Z$.

Examples of alkyl having not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$-$C_{14}$alkyl substituted by $C_1$-$C_8$alkoxy, preferably by $C_1$-$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-$C_1$-$C_4$alkyl)-amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Examples of alkoxy having not more than 18 carbon atoms are methoxy, ethoxy, propoxy, isopropoxy, butocxy, isobutoxy, pentoxy, isopentoxy, hexoxy, heptoxy, octoxy, decyloxy, dodecyloxy, tetradecyloxy, hexadecyloxy and octadecyloxy. Preferred examples of $R_2$ are $C_6$-$C_{12}$alkoxy, in particular heptoxy and octoxy.

Representative examples of the various $C_5$-$C_{12}$cycloalkyl substituents, which are unsubstituted or mono-, di- or tri-substituted by $C_1$-$C_4$alkyl, are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl which is unsubstituted or substituted by $C_1$-$C_4$alkyl is preferred.

Representative examples of $C_5$-$C_{12}$cycloalkoxy $R_2$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having not more than 18 carbon atoms are allyl, 2-methylallyl, hexenyl, decenyl, undecenyl and oleyl. Alkenyl groups in which the carbon atom in the 1-position is saturated are preferred; allyl is particularly preferred.

Examples of substituted phenyl are methylphenyl, dimethylphenyl, trimethylphenyl, t-butylphenyl, di-t-butylphenyl, 3,5-di-t-butyl-4-methylphenyl, methoxyphenyl and ethoxyphenyl.

Representative examples of the various $C_7$-$C_9$phenylalkyl substituents, which are unsubstituted or mono-, di- or tri-substituted on the phenyl by $C_1$-$C_4$alkyl, are benzyl, methylbenzyl, dimethylbenzyl, trimethylbenzyl, t-butylbenzyl and 2-phenylethyl. Benzyl is preferred.

Acyl $R_2$, $R_7$ and Z having not more than 8 carbon atoms can be an aliphatic or aromatic group. Representative examples are formyl, acetyl, propionyl, butyryl, pentanoyl, hexanoyl, heptanoyl, octanoyl, benzoyl, acryloyl or crotonyl. $C_1$-$C_8$alkanoyl, $C_3$-$C_8$alkanoyl and benzoyl are preferred. Acetyl is particularly preferred.

A 5-membered to 7-membered heterocyclic group

can contain a further heteroatom, for example nitrogen or oxygen; representative examples are 1-pyrrolidyl, 1-piperidyl, 4-morpholinyl, 4-methyl-1-piperazinyl and 1-hexahydroazepinyl. 4-Morpholinyl is preferred.

Examples of alkylene having not more than 12 carbon atoms are methylene, ethylene, propylene, trimethylene, tetramethylene, pentamethylene, 2,2-dimethyltrimethylene, hexamethylene, trimethylhexamethylene, octamethylene, decamethylene and dodecamethylene.

Examples of $C_4$-$C_{12}$alkylene interrupted by 1, 2 or 3 oxygen atoms are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl and 3,6,9-trioxaundecane-1,11-diyl.

Representative examples of $C_4$-$C_{12}$alkylene $R_3$, $R_{10}$ and $R_{11}$ interrupted by 1 or 2 >N—$R_7$ groups are the groups

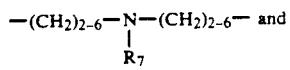

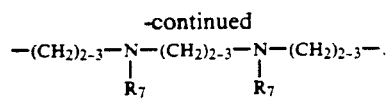

Representative examples of $C_5$-$C_7$cycloalkylene or groups containing 1 or 2 $C_5$-$C_7$cycloalkylene radicals are cyclohexylene, methylcyclohexylene, cyclohexylenedimethylene, methylenedicyclohexylene and isopropylidenedicyclohexylene.

Representative examples of substituted phenylene or groups containing 1 or 2 unsubstituted or substituted phenylene radicals are methylphenylene, dimethylphenylene, xylylene, methylxylylene, methylenediphenylene and isopropylidenediphenylene.

Representative examples of ($C_1$-$C_8$-alkoxy)-carbonyl are methoxycarbonyl, ethoxycarbonyl, propoxycarbonyl, butoxycarbonyl, pentoxycarbonyl, hexoxycarbonyl, heptoxycarbonyl and octoxycarbonyl.

The preferred definitions of $R_2$ are hydrogen, $C_1$-$C_4$alkyl, OH, $C_6$-$C_{12}$alkoxy, $C_5$-$C_8$cycloalkoxy, allyl, benzyl or acetyl, in particular hydrogen or methyl.

Those compounds of the formula (I) are preferred in which $A_1$ is —O— or >N—$R_1$, where $R_1$ is hydrogen, $C_1$-$C_{12}$alkyl, $C_5$-$C_8$cycloalkyl which is unsubstituted or mono-, di- or tri-substituted by $C_1$-$C_4$alkyl; benzyl which is unsubstituted or mono-, di- or tri-substituted on the phenyl by $C_1$-$C_4$alkyl; tetrahydrofurfuryl or a group of the formula (II), $A_2$ is a direct bond or —$CH_2$—, $X_1$ and $X_3$ which can be identical or different are one of the groups of the formulae (IIIa)–(IIIe) in which $A_3$, $A_4$, $A_6$, $A_7$ and $A_8$ which can be identical or different are as defined for $A_1$, $R_3$ is $C_2$-$C_{10}$alkylene, $C_4$-$C_{10}$alkylene interrupted by 1, 2 or 3 oxygen atoms or by 1 or 2 >N—$R_7$ groups where $R_7$ is as defined for $R_1$ or $C_1$-$C_4$acyl or ($C_1$-$C_4$alkoxy)-carbonyl; or cyclohexylene, cyclohexylenedimethylene, methylenedicyclohexylene, isopropylidenedicyclohexylene, phenylene, methylphenylene, xylylene, methylenediphenylene or isopropylidenediphenylene, $R_4$ is hydrogen, $C_1$-$C_4$alkyl or phenyl, $A_5$ is a direct bond or —$CH_2$—, p is zero, 1, 2 or 3, $R_5$ and $R_6$ which can be identical or different are $C_2$-$C_4$alkylene and q is zero or 1, $X_2$ is $C_2$-$C_{10}$alkylene, $C_4$-$C_{10}$alkylene interrupted by 1, 2 or 3 oxygen atoms; 2-hydroxytrimethylene, xylylene or one of the groups of the formulae (IVa)–(IVe) in which $R_8$ is a group of the formula (V) or a group —$OR_{12}$, —$SR_{12}$ or

where $R_{12}$, $R_{13}$ and $R_{14}$ which can be identical or different are hydrogen, $C_1$-$C_{12}$alkyl, $C_5$-$C_8$cycloalkyl which is unsubstituted or mono-, di- or tri-substituted by $C_1$-$C_4$alkyl; $C_3$-$C_{12}$alkenyl, phenyl which is unsubstituted or mono-, di- or tri-substituted by $C_1$-$C_4$alkyl or $C_1$-$C_4$alkoxy; benzyl which is unsubstituted or mono-, di- or tri-substituted on the phenyl by $C_1$-$C_4$alkyl; a group of the formula (II), $C_2$-$C_3$alkyl substituted in the 2- or 3-position by $C_1$-$C_4$alkoxy or by di-($C_1$-$C_4$alkyl)-amino; or the group

is 1-pyrrolidyl, 1-piperidyl, 4-morpholinyl, 4-methyl-1-piperazinyl or 1-hexahydroazepinyl, $R_9$ is a direct bond, $C_1$-$C_{10}$alkylene, cyclohexylene or phenylene, $R_{10}$ is as defined for $R_3$, r is an integer from 1 to 5 and $R_{11}$ is as defined for $R_3$ or is a group

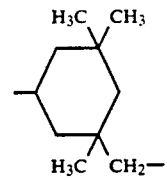

m is zero, 1, 2 or 3, n is a number from 1 to 30, $Y_1$ is Cl, OH, ONa, OK, a group $R_8$ or a group —$X_1Z$ or —$X_3Z$ where Z is hydrogen, methyl, benzyl, $C_1$-$C_4$alcyl or ($C_1$-$C_4$alkoxy)-carbonyl and $Y_2$ is Z, a group

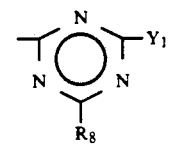

or a group —$X_2OH$.

Those compounds of the formula (I) are particularly preferred in which $A_1$ is —O— or >N—$R_1$, where $R_1$ is hydrogen, $C_1$-$C_8$alkyl, cyclohexyl which is unsubstituted or mono-, di- or tri-substituted by $C_1$-$C_4$alkyl; benzyl, tetrahydrofurfuryl or a group of the formula (II), $A_2$ is a direct bond or —$CH_2$—, $X_1$ and $X_3$ which can be identical or different are one of the groups of the formulae (IIIa)–(IIIe) in which $A_3$, $A_4$, $A_6$, $A_7$ and $A_8$ which can be identical or different are as defined for $A_1$, $R_3$ is $C_2$-$C_8$alkylene, $C_4$-$C_{10}$alkylene interrupted by 1, 2 or 3 oxygen atoms or by an >N—$R_7$ group with $R_7$ being hydrogen, methyl, acetyl or ($C_1$-$C_2$alkoxy)-carbonyl; cyclohexylene, cyclohexylenedimethylene, methylenedicyclohexylene, xylylene or isopropylidenediphenylene, $R_4$ is hydrogen, methyl or phenyl, $A_5$ is a direct bond or —$CH_2$—, p is zero, 1, 2 or 3, $R_5$ and $R_6$ which can be identical or different are $C_2$-$C_3$alkylene and q is zero or 1, $X_2$ is $C_2$-$C_8$alkylene, $C_4$-$C_8$alkylene interrupted by 1 or 2 oxygen atoms; 2-hydroxytrimethylene, xylylene or one of the groups of the formulae (IVa)–(IVe) in which $R_8$ is a group of the formula (V) or a group —$OR_{12}$, —$SR_{12}$ or

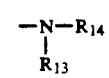

where $R_{12}$, $R_{13}$ and $R_{14}$ which can be identical or different are hydrogen, $C_1$-$C_8$alkyl, cyclohexyl which is unsubstituted or mono-, di- or tri-substituted by $C_1$-$C_4$alkyl; allyl, undecenyl, phenyl, benzyl, a group of the formula (II), $C_2$-$C_3$alkyl substituted in the 2- or 3-position by $C_1$-$C_4$alkoxy, by dimethylamino or by diethylamino; or the group

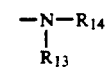

is 4-morpholinyl, $R_9$ is a direct bond, $C_1$-$C_8$alkylene, cyclohexylene or phenylene, $R_{10}$ is $C_2$-$C_8$alkylene, $C_4$-$C_{10}$alkylene interrupted by 1, 2 or 3 oxygen atoms; cyclohexylenedimethylene, isopropylidenedicyclohexylene or isopropylidenediphenylene, r is an integer from 1 to 4, $R_{11}$ is as defined for $R_3$ or is methylphenylene, methylenediphenylene or a group

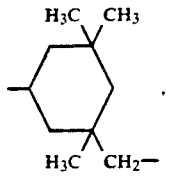

m is zero, 1, 2 or 3, n is a number from 1 to 20, $Y_1$ is OH, ONa, OK, a group $R_8$ or a group —$X_1Z$ or —$X_3Z$ where Z is hydrogen, methyl, acetyl or ($C_1$-$C_2$alkoxy)-carbonyl and $Y_2$ is Z, a group

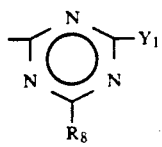

or a group —$X_2$OH.

Those compounds of the formula (I) are of special interest in which $A_1$ is —O— or >N—$R_1$, where $R_1$ is hydrogen, $C_1$-$C_4$alkyl, cyclohexyl, benzyl or a group of the formula (II), $A_2$ is a direct bond or —$CH_2$—, $X_1$ and $X_3$ which can be identical or different are one of the groups of the formulae (IIIa)-(IIIe) in which $A_3$, $A_4$, $A_6$, $A_7$ and $A_8$ which can be identical or different are as defined for $A_1$, $R_3$ is $C_2$-$C_6$alkylene, $C_6$-$C_{10}$alkylene interrupted by 2 or 3 oxygen atoms; cyclohexylenedimethylene, methylenedicyclohexylene or xylylene, $R_4$ is hydrogen or methyl, $A_5$ is a direct bond, p is zero or 1, $R_5$ and $R_6$ are ethylene or trimethylene and q is zero or 1, $X_2$ is $C_2$-$C_6$alkylene, 2-hydroxytrimethylene, xylylene or one of the groups of the formulae (IVa)-(IVe) in which $R_8$ is a group of the formula (V) or a group —$OR_{12}$ or

in which $R_{12}$ is $C_1$-$C_4$alkyl, cyclohexyl, allyl, phenyl, benzyl or a group of the formula (II), $R_{13}$ and $R_{14}$ which can be identical or different are as defined above for $R_{12}$ or are hydrogen or $C_2$-$C_3$alkyl substituted in the 2- or 3-position by methoxy, by ethoxy, by dimethylamino or by diethylamino; or the group

is 4-morpholinyl, $R_9$ is a direct bond or $C_1$-$C_8$alkylene, $R_{10}$ is $C_4$-$C_6$alkylene, r is 1 or 2, $R_{11}$ is $C_2$-$C_6$alkylene or a group

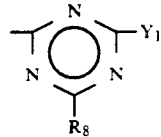

m is zero, 1 or 2, n is a number from 1 to 15, $Y_1$ is OH, ONa, OK, a group $R_8$ or a group —$X_1Z$ or $X_3Z$ where Z is hydrogen, methyl, acetyl or ($C_1$-$C_2$alkoxy)-carbonyl and $Y_2$ is Z, a group

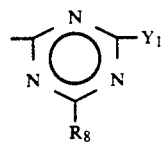

or a group —$X_2$OH.

Those compounds of the formula (I) are of particular interest in which $A_1$ is —O— or >N—$R_1$, where $R_1$ is hydrogen, methyl, 2,2,6,6-tetramethyl-4-piperidyl or 1,2,2,6,6-pentamethyl-4-piperidyl, $A_2$ is a direct bond or —$CH_2$—, $X_1$ and $X_3$ which can be identical or different are a group of the formula (IIIa) or (IIIb) in which $A_3$ and $A_4$ which can be identical or different are an >N—$R_1$ group where $R_1$ is as defined above, $R_3$ is —$(CH_2)_{2-6}$— or —$(CH_2)_3$—O—$(CH_2)_{2-4}$—O—$(CH_2)_3$— and $R_4$ is hydrogen or methyl, $X_2$ is 2-hydroxytrimethylene or a group of the formula (IVa) where $R_8$ is a group of the formula (V), m is zero or 1, n is a number from 1 to 10, $Y_1$ is OH, ONa, OK, a group $R_8$ or a group —$X_1Z$ or —$X_3Z$ with Z being hydrogen or methyl and $Y_2$ is hydrogen, methyl or a group

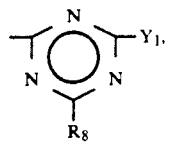

with the proviso that $X_1$ or $X_2$ or $X_3$ contains a group of the formula (II) with $R_2$ being hydrogen or methyl.

The compounds of the present invention can be prepared by processes known per se, for example as described in U.S. Pat. Nos. 4,086,204, 4,459,395 and 4,547,548, by reacting, in any order and according to the appropriate molar ratios, cyanuric chloride with compounds of the formulae (VIa), (VIb), (VIc) or (VId)

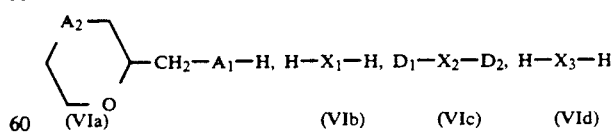

in which $A_1$, $A_2$, $X_1$, $X_2$ and $X_3$ are as defined above and $D_1$ and $D_2$ are e.g. Cl, Br, methoxy or ethoxy or $D_1$—$X_2$—$D_2$ is epichlorohydrin or a diisocyanate OCN—$R_{11}$—NCO with $R_{11}$ being as defined above.

The compounds of the formulae (VIa), (VIb), (VIc) and (VId) are commercially available or can easily be prepared by known processes.

As mentioned at the outset, the novel compounds of the present invention are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1l), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylideneorbornene; as well as mixtures of such copolymers and their mixtures with polymers mentioned in 1)above, for example polypropylene/ethylene-propylene copolymers, LDPE/EVA, LDPE/EAA, LLDPE/EVA and LLDPE/EAA.

3a. Copolymers of α-olefins with carbon monoxide, with regular or random alternation.

3b. Hydrocarbon resins (for example $C_5$–$C_9$l) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from copolymers of styrene and other polymers, such as, for example, from a polyacrylate, a diene polymer or an ethylene/propylene/diene terpolymer and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene; styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene; styrene and alkyl acrylates or methacrylates on polybutadiene; styrene and acrylonitrile on ethylene/propylene/diene terpolymers; styrene and acrylonitrile on polyacrylates or polymethacrylates; styrene and acrylonitrile on acrylate/butadiene copolymers as well as mixtures thereof with the copolymers listed under 5), for instance the mixtures known as ABS, MBS, ASA and AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, such as for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene and polyamides.

14. Polyurethanes which are derived from polyethers, polyesters or polybutadiene with terminal hydroxyl groups on the one hand and aliphatic or aromatic polyisocyanates on the other hand, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6/6, polyamide 6/10, 6/9, 6/12 and 4/6, polyamide 11, polyamide 12, aromatic polyamides obtained by condensation of m-xylenediamine and adipic acid; polyamides prepared from hexamethylenediamine and isophthalic and/or terephthalic acid and optionally an elastomer as modifier, for example poly-2,4,4-trimethyl-hexamethyleneterephthalamide or poly-m-phenylene-isophthalamide. Further, copolymers of the aforementioned polyamides with polyolefins, olefin copolymers, ionomers or chemically bonded or grafted elastomers; or with polyethers, as, for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane] terephthalate and polyhydroxybenzoate as well as block copolyether-esters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of the polymers mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6/6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratio, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably between 0.05 and 1%.

In general, the compounds of the formula (I) can be added to the polymeric materials before, during or after the polymerization or crosslinking of the said materials.

The compounds of the formula (I) can be incorporated in the polymeric materials in the pure form or encapsulated in waxes, oils or polymers.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the formula (I) can be used for the production of mouldings, films, tapes, monofilaments, fibers, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in admixture with the compounds of the formula (I) are:

1. ANTIOXIDANTS 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl) phenol], 2,2'-methylenebis(4-methyl-6-cyclohexylphenol), 2,2'-methylenebis (6-nonyl-4-methylphenol), 2,2'-methylenebis(4,6-di-tert-butylphenol), 2,2'-ethylidenebis (4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis (6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)-butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.8. Esters of α-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'bis(hydroxyethyl)oxamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxamide.

1.10. Amides of β-(3,5-di-tert-butyl-4-hydroxyphenyl)propionic acid e.g.
N,N'-bis(3,5-di-tert-butyl-4-hydroxyphenylpropionyl)-hexamethylenediamine,
N,N'-bis(3,5-di-tert-butyl-4-hydroxyphenylpropionyl)-trimethylenediamine,
N,N'-bis(3,5-di-tert-butyl-4-hydroxyphenylpropionyl)-hydrazine.

2. UV ABSORBERS AND LIGHT STABILIZERS 2.1 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis-( α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of variously substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylatesk, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl) phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone).

2.7. Oxalic acid-diamides, for example, 4,4'-dioctyloxyoxanilide, 2,2'-dioctyloxy-5,5'-di -tert-butyloxanilide, 2,2'-didodecyloxy-5,5'-di-tert-butyloxanilide, 2-ethoxy-2'-ethyloxanilide, N,N'-bis(3-dimethylaminopropyl)oxamide, 2-ethoxy-5-tert-butyl-2'-ethyloxanilide and its mixtures with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxyl-4-dodecyloxyphenyl)-4,6-bis(2,4-dimethylphenyl)-1,3,5-triazine.

3. Metal deactivators, for example N,N'-diphenyloxamide, N-salicyla-N'-salicyloylhydrazine, N,N'-bis(-salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-diphosphaspiro[5.5]undecane.

4a. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis-(1-hydroxy-2,2,6,6-tetramethyl-4-piperidyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flame-proofing agents, antistatic agents and blowing agents.

The compounds of the invention can also be used as stabilizers, especially as light stabilizers, for almost all materials known in the art of photographic reproduction and other reproduction techniques as e.g. described in Research Disclosure 1990, 31429 (pages 474 to 480).

Several examples of the preparation of the compounds of the formula (I) are reported for more detailed illustration of the present invention; these examples are given solely for illustrative purposes and do not imply any restriction.

The compounds of Examples 1, 2, 5, 6 and 7 reveal a particularly preferred embodiment of the instant invention.

The number-average molecular weight given in the examples which follow is determined by the method described in European laid Open Print 255,990 from page 18, line 54, to page 19, line 15.

EXAMPLE 1

18.44 g (00.1 mol) of cyanuric chloride, 14.30 g (0.14 mol) of tetrahydrofurfuryl alcohol, 11.09 g (0.132 mol) of sodium bicarbonate and 130 ml of xylene are heated at 100° C. for 6 hours.

After cooling to ambient temperature, 47.36 g (0.12 mol) of N,N'-bis-(2,2,6,6-tetramethyl-4-piperidyl)-1,6-hexanediamine and 12.12 g (0.1 mol) of 33% sodium hydroxide are added and the mixture is heated at 60° C. for 4 hours.

8 g (0.2 mol) of ground sodium hydroxide are added and the mixture is heated under reflux with removal of the water and part of the solvent in such a way that an internal temperature of 155° C. is reached for 10 hours and this temperature is then maintained for 4 hours.

After cooling to about 70° C. and dilution with 150 ml of xylene, the reaction mixture is filtered and evaporated in vacuo.

This gives a compound having a melting point of 151°–160° C. and a molecular weight of $\overline{M}n=2260$, containing recurring units of the formula

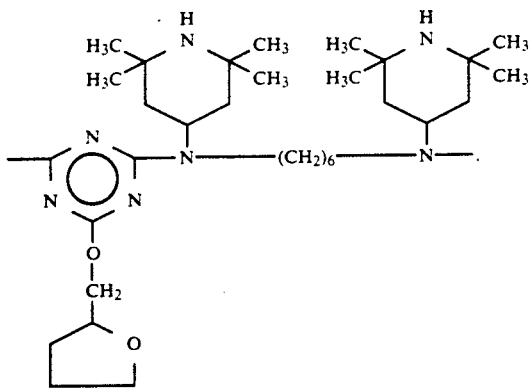

EXAMPLE 2

Following the procedure described in Example 1, but using 16.26 g (0.14 mol) of tetrahydropyran-2-methanol in place of the tetrahydrofurfuryl alcohol, a compound having a melting point of 97°–102° C. and molecular weight of $\overline{M}n=1900$, containing recurring units of the formula

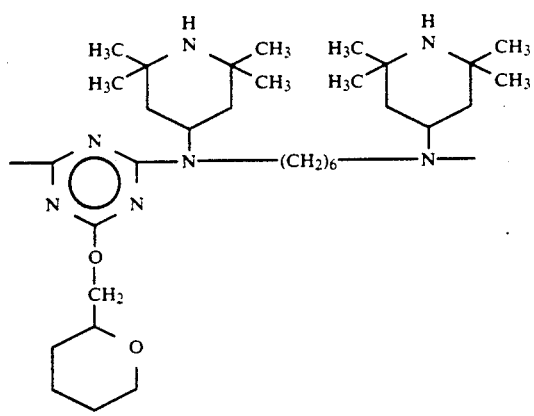

is obtained.

EXAMPLE 3

A solution of 10.11 g (0.1 mol) of tertrahydrofurfurylamine in 40 ml of xylene is slowly added to a solution of 18.44 g (0.1 mol) of cyanuric chloride in 200 ml of xylene, maintaining the temperature at between −30° and −10° C.

After one hour at between −10° and 0° C., 12.12 g (0.1 mol) of 33% sodium hydroxide are added slowly, maintaining the temperature at 0° C.

The mixture is stirred for 1 hour at between 0° and 20° C., 47.36 g (0.12 mol) of N,N'-bis-(2,2,6,6-tetramethyl-4-piperidyl)-1,6-hexanediamine and 12.12 g (0.1 mol) of 33% sodium hydroxide are added and the mixture is heated at 90° C. for 2 hours.

8 g (0.2 mol) of ground sodium hydroxide are added and the mixture is heated under reflux with removal of the water and part of the solvent in such a way that an internal temperature of 155° C. is reached for 10 hours and this temperature is then maintained for 4 hours.

After cooling to about 70° C. and dilution with 150 ml of xylene, the reaction mixture is filtered and evaporated in vacuo.

This gives a compound having a melting point of 156°-163° C. and a molecular weight of $\overline{M}n=1700$, containing recurring units of the formula

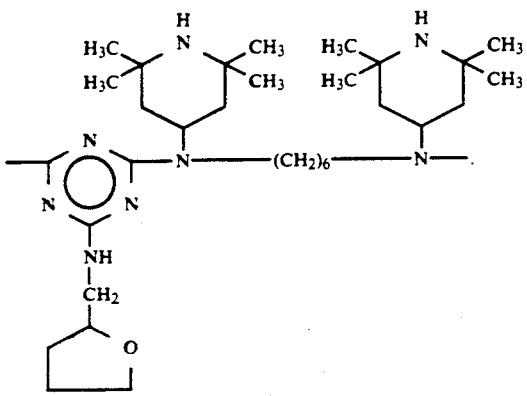

EXAMPLE 4

Following the procedure described in Example 3, but using 54.57 g (0.12 mol) of N,N'-bis-(2,2,6,6-tetramethyl-4-piperidyl)-4,7-dioxadecane-1,10-diamine in place of the N,N'-bis-(2,2,6,6-tetramethyl-4-piperidyl)-1,6-hexanediamine, a compound having a melting point of 88°-92° C. and a molecular weight of $\overline{M}n=1800$, containing recurring units of the formula

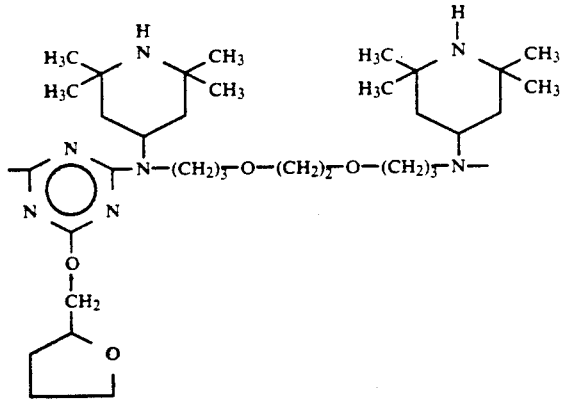

is obtained.

EXAMPLE 5

A solution of 24.04 g (0.1 mol) of N-(2,2,6,6-tetramethyl-4-piperidyl)-tetrahydrofurfurylamine in 40 ml of xylene is slowly added to a solution of 18.44 g (0.1 mol) of cyanuric chloride in 200 ml of xylene, maintaining the temperature at about −10° C.

The mixture is stirred for 1 hour at between −10° and 10° C. and 12.12 g (0.1 mol) of 33% sodium hydroxide are then added slowly, maintaining the temperature at 10° C.

After one hour at this temperature, 49.34 g (0.125 mol) of N,N'-bis-(2,2,6,6-tetramethyl-4-piperidyl)-1,6-hexanediamine and 12.12 g (0.1 mol) of 33% sodium hydroxide are added and the mixture is heated at 90° C. for 2 hours.

8 g (0.2 mol) of ground sodium hydroxide are added and the mixture is heated under reflux with removal of the water and part of the solvent in such a way that an internal temperature of 155° C. is reached after 10 hours and this temperature is then maintained for 4 hours. After cooling to about 70° C. and dilution with 150 ml of xylene, the reaction mixture if filtered and evaporated in vacuo. This gives a compound having a melting point of 140°-148° C. and a molecular weight of $\overline{M}n=2570$, containing recurring units of the formula

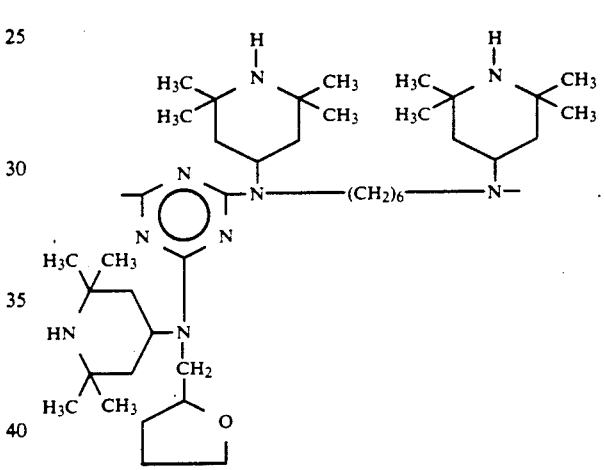

EXAMPLE 6

38.83 g (0.1 mol) of 2,4-dichloro-6-[N-(2,2,6,6-tetramethyl-4-piperidyl) tetrahydrofurfurylamino]-1,3,5-triazine, 23.68 g (0.06 mol) of N,N'-bis-(2,2,6,6-tetramethyl-4-piperidyl)-1,6-hexanediamine, 12.08 g (0.06 mol) of 1-(2-hydroxyethyl)-2,2,6,6-tetramethyl-4-piperidinol, 12.12 g (0.1 mol) of 33% sodium hydroxide and 200 ml of xylene are heated at 90° C. for 2 hours.

8 g (0.2 mol) of ground sodium hydroxide are added and the mixture is heated under reflux with removal of the water and part of the solvent in such a way that an internal temperature of 160° C. is reached after 10 hours and this temperature is then maintained for 4 hours.

After cooling to about 70° C. and dilution with 150 ml of xylene, the reaction mixture is filtered and evaporated under reduced pressure.

This gives a compound having a melting point of 150°-156° C. and a molecular weight of $\overline{M}n=2000$, containing recurring units of the formula

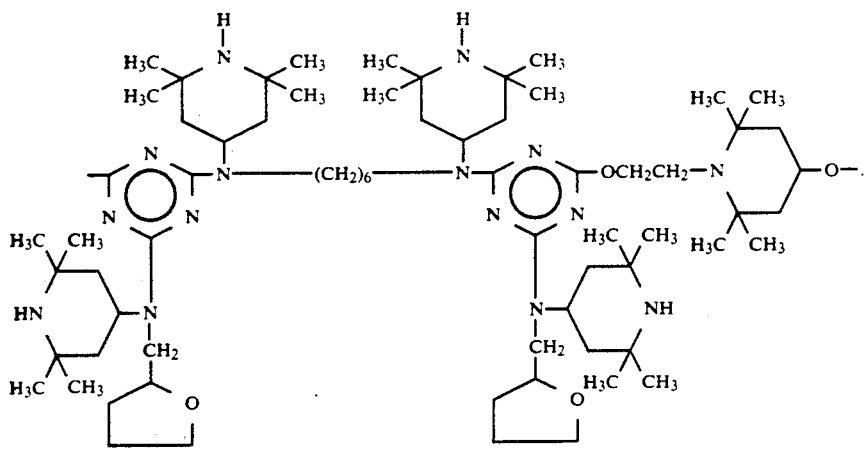

EXAMPLE 7

18.44 g (0.1 mol) of cyanuric chloride, 14.30 g (0.14 mol) of tetrahydrofurfuryl alcohol, 11.09 g (0.132 mol) of sodium bicarbonate and 200 ml of xylene are heated at 100° C. for 6 hours. After cooling to ambient temperature, 22.10 g (0.056 mol) of N,N'-bis-(2,2,6,6-tetramethyl-4-piperidyl)-1,6-hexanediamine, 6.51 g (0.056 mol) of 1,6-hexanediamine and 12.12 g (0.1 mol) of 33% sodium hydroxide are added and the mixture is heated for 2 hours at 90° C.

8 g (0.2 mol) of ground sodium hydroxide are added and the mixture is heated under reflux with removal of the water and part of the solvent in such a way that an internal temperature of 155° C. is reached after 10 hours and this temperature is then maintained for 4 hours.

After cooling to about 70° C. and dilution with 150 ml of xylene, the reaction mixture is filtered and evaporated under reduced pressure.

This gives a compound having a melting point of 191°-196° C. and a molecular weight of $\overline{M}n=3000$, containing recurring units of the formula

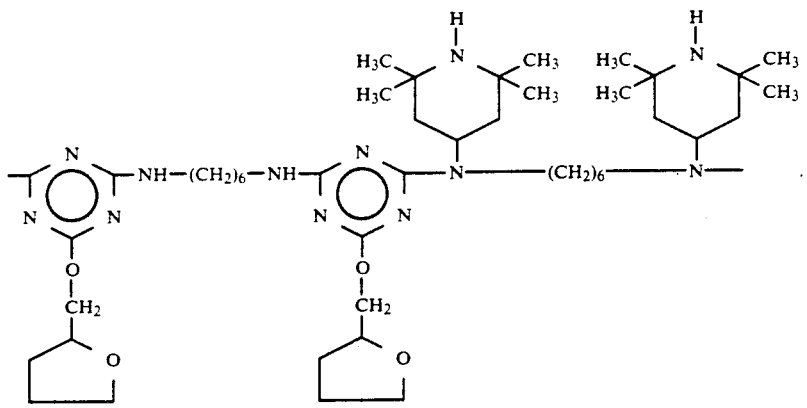

EXAMPLE 8

25/01 g (0.1 mol) of 2,4-dichloro-6-tetrahydrofurfuryloxy-1,3,5-triazine, 88.80 g (0.225 mol) of N,N'-bis-(2,2,6,6-tetramethyl-4-piperidyl)-1,6-hexanediamine, 9.25 g (0.1 mol) of epichlorohydrin and 110 ml of 4-methyl-2-pentanol are heated under reflux for 12 hours, while slowly adding 16.5 g (0.412 mol) of sodium hydroxide during the last 10 hours of reaction. After the end of the sodium hydroxide addition, the reaction mixture is heated under reflux for 2 hours, diluted with 200 ml of xylene and filtered.

The filtrate is evaporated under reduced pressure, which gives a compound having a melting point of 77°-81° C. and a molecular weight of $\overline{M}n=2130$, containing recurring units of the formula

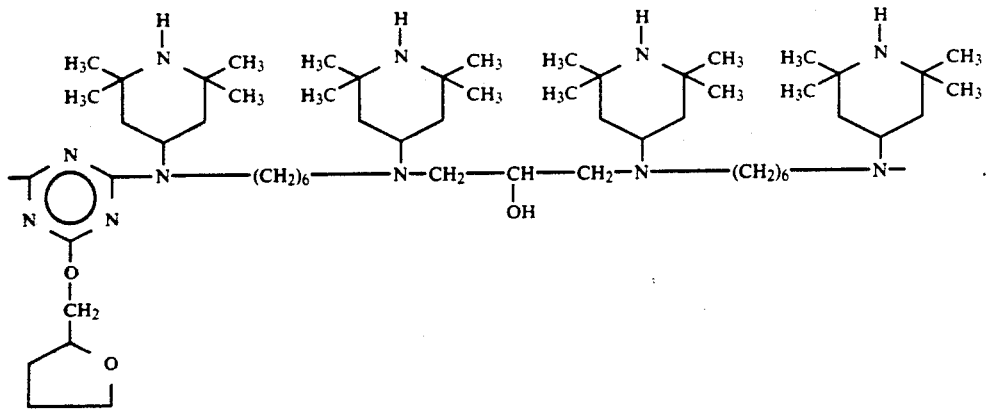

The efficacy of the compounds of the present invention as stabilizers is illustrated in the following example in which some compounds obtained in the preparation examples are used for stabilizing polypropylene fibres.

EXAMPLE 9

(Light-stabilizing action in polypropylene fibers)

2.5 g of each of the products indicated in Table 1, 1.0 g of tris-(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index=12 g/10 minutes (measured at $230°$ C. and 2.16 kg).

The mixtures are extruded at $200°-230°$ C. to give polymer granules which are then converted into fibers, using a pilot-type apparatus (®Leonard, Sumirago (VA), Italy) and operating under the following conditions:

| extruder temperature | $200-230°$ C. |
|---|---|
| head temperature | $255-260°$ C. |
| stretch ratio | 1:3.5 |
| count | 11 dtex per filament. |

The fibers thus prepared are exposed, mounted on a white card, in a model 65 WR Weather-O-Meter (ASTM D 2565-85) with a black panel temperature of $63°$ C.

The residual tenacity is measured on samples taken after various times of exposure to light by means of a constant-speed tensometer, and the exposure time in hours ($T_{50}$) needed to halve the initial tenacity is then calculated.

Fibres prepared under the same conditions as indicated above, but without addition of the compounds of the invention, are exposed for comparison.

The results obtained are shown in Table 1:

TABLE 1

| Stabilizer | $T_{50}$ (hours) |
|---|---|
| None | 150 |
| Compound from Example 1 | 1160 |
| Compound from Example 2 | 1220 |
| Compound from Example 4 | 1230 |
| Compound from Example 6 | 1500 |
| Compound from Example 8 | 1400 |

What is claimed:
1. A compound of the formula (I)

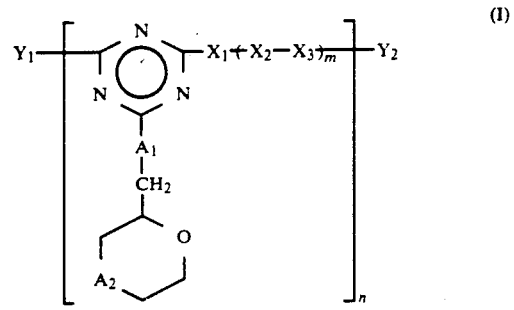

in which $A_1$ is —O— or >N—$R_1$, in which $R_1$ is hydrogen, $C_1$-$C_{18}$alkyl, $C_5$-$C_{12}$cycloalkyl which is unsubstituted or mono-, di- or tri-substituted by $C_1$-$C_4$alkyl; $C_7$-$C_9$phenylalkyl which is unsubstituted or mono-, di- or tri-substituted on the phenyl by $C_1$-$C_4$alkyl; tetrahydrofurfuryl or a group of the formula (II)

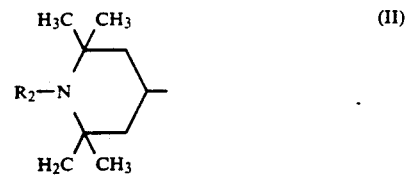

in which $R_2$ is hydrogen, $C_1$-$C_8$alkyl, O•, OH, NO, CH$_2$CN, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di- or tri-substituted on the phenyl by $C_1$-$C_4$alkyl; or $R_2$ is $C_1$-$C_8$acyl, $A_2$ is a direct bond or —CH$_2$—, $X_1$ and $X_3$ which can be identical or different are one of the groups of the formulae (IIIa)–(IIIe)

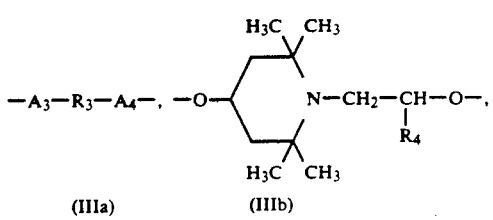

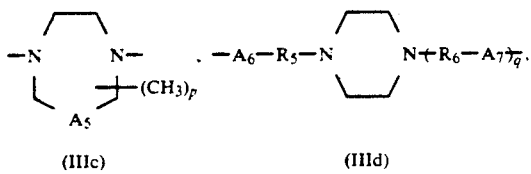

(IIIc)  (IIId)

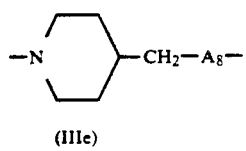

(IIIe)

in which $A_3$, $A_4$, $A_6$, $A_7$ and $A_8$ which can be identical or different are as defined for $A_1$, $R_3$ is $C_2$–$C_{12}$alkylene, $C_4$–$C_{12}$alkylene interrupted by 1, 2 or 3 oxygen atoms or by 1 or 2 >N—$R_7$ groups, where $R_7$ is as defined for $R_1$ or is $C_1$–$C_8$acyl or ($C_1$–$C_8$alkoxy)-carbonyl; or $C_5$–$C_7$cycloalkylene, $C_5$–$C_7$cycloalkylene-di-($C_1$–$C_4$alkylene), $C_1$–$C_4$alkylene-di-($C_5$–$C_7$-cycloalkylene), $C_2$–$C_4$alkylidene-di-($C_5$–$C_7$cycloalkylene), phenylene, phenylene-di-($C_1$–$C_4$alkylene), $C_1$–$C_4$alkylenediphenylene or $C_2$–$C_4$alkylidenediphenylene, it being possible for each phenylene group to be unsubstituted or mono- or di-substituted by $C_1$–$C_4$alkyl, $R_4$ is hydrogen, $C_1$–$C_8$alkyl or phenyl, $A_5$ is a direct bond or —$CH_2$—, p is zero, 1, 2 or 3, $R_5$ and $R_6$ which can be identical or different are $C_2$–$C_6$alkylene and q is zero or 1, $X_2$ is $C_2$–$C_{12}$alkylene, $C_4$–$C_{12}$alkylene interrupted by 1, 2 or 3 oxygen atoms; 2-hydroxytrimethylene, xylylene, carbonyl or one of the groups of the formulae (IVa)–(IVe)

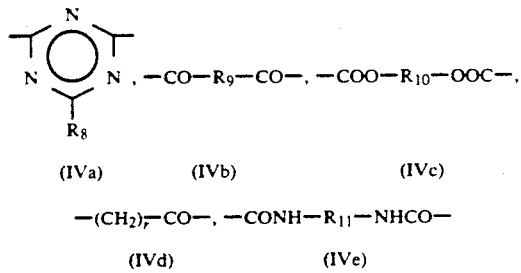

(IVa)  (IVb)  (IVc)

—($CH_2$)$_r$—CO—, —CONH—$R_{11}$—NHCO—

(IVd)  (IVe)

in which $R_8$ is a group of the formula (V)

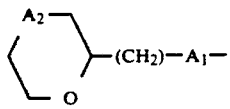

(V)

with $A_1$ and $A_2$ as defined above, or $R_8$ is a group —$OR_{12}$, —$SR_{12}$ or

in which $R_{12}$, $R_{13}$ and $R_{14}$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl; $C_3$–$C_{18}$alkenyl, phenyl which is unsubstituted or mono-, di- or tri-substituted by $C_1$–$C_4$alkyl or $C_1$–$C_4$alkoxy; $C_7$–$C_9$phenylalkyl which is unsubstituted or mono-, di- or tri-substituted on the phenyl by $C_1$–$C_4$alkyl; a group of the formula (II), $C_2$–$C_4$alkyl substituted in the 2-, 3- or 4-position by $C_1$–$C_8$alkoxy or by di-($C_1$–$C_4$alkyl)-amino; or the group

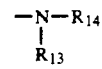

is a 5-membered to 7-membered heterocyclic group, $R_9$ is a direct bond, $C_1$–$C_{12}$alkylene, cyclohexylene, methycyclohexylene or phenylene, $R_{10}$ is as defined for $R_3$, r is an integer from 1 to 10 and $R_{11}$ is as defined for $R_3$ or a group

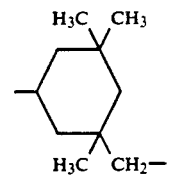

m is zero, 1, 2, 3 or 4, n is a number from 1 to 50, $Y_1$ is Cl, OH, ONa, OK, a group $R_8$ or a group —$X_1Z$ or —$X_3Z$ where Z is hydrogen, methyl, benzyl, $C_1$–$C_8$acyl or ($C_1$–$C_8$alkoxy)-carbonyl and $Y_2$ is Z, a group

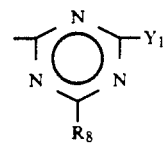

or a group —$X_2OH$; the provisos applying to the compounds of the formula (I) that (1l) $X_1$ or $X_2$ or $X_3$ contains a group of the formula (II), that (2l) each of the groups $A_1$, $A_2$, $X_1$, $X_2$, $X_3$ and m has the same or a different definition in the individual recurring structural units of the formula (I) and that (3l), when m is zero and n is 1, the only definition of $Y_1$ is the group —$X_1Z$.

2. A compound of the formula (I) according to claim 1, in which $R_2$ is hydrogen, $C_1$–$C_4$alkyl, OH, $C_6$–$C_{12}$alkoxy, $C_5$–$C_8$cycloalkoxy, allyl, benzyl or acetyl.

3. A compound of the formula (I) according to claim 1, in which $A_1$ is —O— or >N—$R_1$, where $R_1$ is hydrogen, $C_1$–$C_{12}$alkyl, $C_5$–$C_8$cycloalkyl which is unsubstituted or mono-, di- or tri-substituted by $C_1$–$C_4$alkyl; benzyl which is unsubstituted or mono-, di- or tri-substituted on the phenyl by $C_1$–$C_4$alkyl; tetrahydrofurfuryl or a group of the formula (II), $A_2$ is a direct bond or —$CH_2$—, $X_1$ and $X_3$ which can be identical or different are one of the groups of the formulae (IIIa)–(IIIe) in which $A_3$, $A_4$, $A_6$, $A_7$ and $A_8$ which can be identical or different are as defined for $A_1$, $R_3$ is $C_2$–$C_{10}$alkylene, $C_4$–$C_{10}$alkylene interrupted by 1, 2 or 3 oxygen atoms or by 1 or 2>N—$R_7$ groups where $R_7$ is as defined for $R_1$ or $C_1$–$C_4$acyl or ($C_1$–$C_4$alkoxy)-carbonyl; or cyclohexylene, cyclohexylenedimethylene, methylenedicyclohexylene, isopropylidenedicyclohexylene, phenylene, methylphenylene, xylylene, methylenediphenylene or isopropylidenediphenylene, $R_4$ is hydrogen, $C_1$–$C_4$alkyl or phenyl, $A_5$ is a direct bond or —$CH_2$—, p is zero, 1, 2 or 3, $R_5$ and $R_6$ which can be identical or different are $C_2$–$C_4$alkylene and q is zero or 1, $X_2$ is $C_2$–$C_{10}$alkylene, $C_4$–$C_{10}$alkylene interrupted by 1, 2 or 3 oxygen atoms; 2-hydroxytrimethylene, xylylene or one of the groups of the formulae (IVa)–(IVe) in which $R_8$ is a group of the formula (V) or a group —$OR_{12}$, —$SR_{12}$ or

where $R_{12}$, $R_{13}$ and $R_{14}$ which can be identical or different are hydrogen, $C_1$-$C_{12}$alkyl, $C_5$-$C_8$cycloalkyl which is unsubstituted or mono-, di- or tri-substituted by $C_1$-$C_4$alkyl; $C_3$-$C_{12}$alkenyl, phenyl which is unsubstituted or mono-, di- or tri-substituted by $C_1$-$C_4$alkyl or $C_1$-$C_4$alkoxy; benzyl which is unsubstituted or mono-, di- or tri-substituted on the phenyl by $C_1$-$C_4$alkyl; a group of the formula (II), $C_2$-$C_3$alkyl substituted in the 2- or 3-position by $C_1$-$C_4$alkoxy or by di-($C_1$-$C_4$alkyl)-amino; or the group

is 1-pyrrolidyl, 1-piperidyl, 4-morpholinyl, 4-methyl-1-piperazinyl or 1-hexahydroazepinyl, $R_9$ is a direct bond, $C_1$-$C_{10}$alkylene, cyclohexylene or phenylene, $R_{10}$ is as defined for $R_3$, r is an integer from 1 to 5 and $R_{11}$ is as defined for $R_3$ or is a group

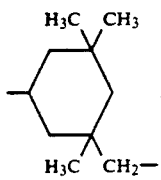

m is zero, 1, 2 or 3, n is a number from 1 to 30, $Y_1$ is Cl, OH, ONa, OK, a group $R_8$ or a group —$X_1Z$ or —$X_3Z$ where Z is hydrogen, methyl, benzyl, $C_1$-$C_4$acyl or 1($C_1$-$C_4$alkoxy)-carbonyl and $Y_2$ is Z, a group

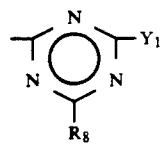

or a group —$X_2OH$.

4. A compound of the formula (I) according to claim 1, in which $A_1$ is —O— or >N—$R_1$, where $R_1$ is hydrogen, $C_1$-$C_8$alkyl, cyclohexyl which is unsubstituted or mono-, di- or tri-substituted by $C_1$-$C_4$alkyl; benzyl, tetrahydrofurfuryl or a group of the formula (II), $A_2$l is a direct bond or —$CH_2$—, $X_1$ and $X_3$ which can be identical or different are one of the groups of the formulae (IIIa)–(IIIe) in which $A_3$, $A_4$, $A_6$, $A_7$ and $A_8$ which can be identical or different are as defined for $A_1$, $R_3$ is $C_2$-$C_8$alkylene, $C_4$-$C_{10}$alkylene interrupted by 1, 2 or 3 oxygen atoms or by an >N—$R_7$ group with $R_7$ being hydrogen, methyl, acetyl or ($C_1$-$C_2$alkoxy)-carbonyl; cyclohexylene, cyclohexylenedimethylene, methylenedicyclohexylene, xylylene or isopropylidenediphenylene, $R_4$ is hydrogen, methyl or phenyl, $A_5$ is a direct bond or —$CH_2$—, p is zero, 1, 2 or 3, $R_5$ and $R_6$ which can be identical or different are $C_2$-$C_3$alkylene and q is zero or 1, $X_2$ is $C_2$-$C_8$alkylene, $C_4$-$C_8$alkylene interrupted by 1 or 2 oxygen atoms; 2-hydroxytrimethylene, xylylene or one of the groups of the formulae (IVa)–(IVe) in which $R_8$ is a group of the formula (V) or a group —$OR_{12}$, —$SR_{12}$ or

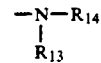

where $R_{12}$, $R_{13}$ and $R_{14}$ which can be identical or different are hydrogen, $C_1$-$C_8$alkyl, cyclohexyl which is unsubstituted or mono-, di- or tri-substituted by $C_1$-$C_4$alkyl; allyl, undecenyl, phenyl, benzyl, a group of the formula (II), $C_2$-$C_3$alkyl substituted in the 2- or 3-position by $C_1$-$C_4$alkoxy, by dimethylamino or by diethylamino; or the group

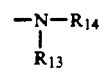

is 4-morpholinyl, $R_9$ is a direct bond, $C_1$-$C_8$alkylene, cyclohexylene or phenylene, $R_{10}$ is $C_2$-$C_8$alkylene, $C_4$-$C_{10}$alkylene interrupted by 1, 2 or 3 oxygen atoms; cyclohexylenedimethylene, isopropylidenedicyclohexylene or isopropylidenediphenylene, r is an integer from 1 to 4, $R_{11}$ is as defined for $R_3$ or is methylphenylene, methylenediphenylene or a group

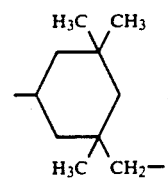

m is zero, 1, 2 or 3, n is a number from 1 to 20, $Y_1$ is OH, ONa, OK, a group $R_8$ or a group —$X_1Z$ or —$X_3Z$ where Z is hydrogen, methyl, acetyl or ($C_1$-$C_2$alkoxyl)-carbonyl and $Y_2$ is Z, a group

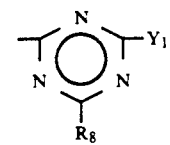

or a group —$X_2OH$.

5. A compound of the formula (I) according to claim 1, in which $A_1$ is —O— or >N—$R_1$, where $R_1$ is hydrogen, $C_1$-$C_4$alkyl, cyclohexyl, benzyl or a group of the formula (II), $A_2$ is a direct bond or —$CH_2$—, $X_1$ and $X_3$ which can be identical or different are one of the groups of the formulae (IIIa)–(IIIe) in which $A_3$, $A_4$, $A_6$, $A_7$ and $A_8$ which can be identical or different are as defined for $A_1$, $R_3$ is $C_2$-$C_6$alkylene, $C_6$-$C_{10}$alkylene interrupted by 2 or 3 oxygen atoms; cyclohexylenedimethylene, methylenedicyclohexylene or xylylene, $R_4$ is hydrogen or methyl, $A_5$ is a direct bond, p is zero or 1, $R_5$ and $R_6$ are ethylene or trimethylene and q is zero or 1, $X_2$ is $C_2$-$C_6$alkylene, 2-hydroxytrimethylene, xylylene or one of the groups of the formulae (IVa)–(IVe) in which $R_8$ is a group of the formula (V) or a group —$OR_{12}$ or

in which $R_{12}$ is $C_1$-$C_4$alkyl, cyclohexyl, allyl, phenyl, benzyl or a group of the formula (II), $R_{13}$ and $R_{14}$ which can be identical or different are as defined above for $R_{12}$ or are hydrogen or $C_2$-$C_3$alkyl substituted in the 2- or 3-position by methoxy, by ethoxy, by dimethylamino or by diethylamino; or the group

is 4-morpholinyl, $R_9$ is a direct bond or $C_1$-$C_8$alkylene, $R_{10}$ is $C_4$-$C_6$alkylene, r is 1 or 2, $R_{11}$ is $C_2$-$C_6$alkylene or a group

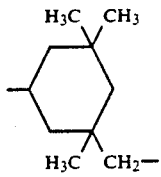

m is zero, 1 or 2, n is a number from 1 to 15, $Y_1$ is OH, ONa, OK, a group $R_8$ or a group $-X_1Z$ or $-X_3Z$ where Z is hydrogen, methyl, acetyl or ($C_1$-$C_2$alkoxy)-carbonyl and $Y_2$ is Z, a group

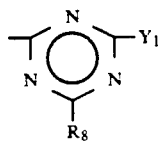

or a group $-X_2OH$.

6. A compound of the formula (I) according to claim 1, in which $A_1$ is $-O-$ or $>N-R_1$, where $R_1$ is hydrogen, methyl, 2,2,6,6-tetramethyl-4-piperidyl or 1,2,2,6,6-pentamethyl-4-piperidyl, $A_2$ is a direct bond or $-CH_2-$, $X_1$ and $X_3$ which can be identical or different are a group of the formula (IIIa) or (IIIb) in which $A_3$ and $A_4$ which can be identical or different are an $>N-R_1$ group where $R_1$ is as defined above, $R_3$ is $-(CH_2)_{2-6}-$ or $-(CH_2l)_3-O-(CH_2l)_{2-4}-O-(CH_2)_3-$ and $R_4$ is hydrogen or methyl, $X_2$ is 2-hydroxytrimethylene or a group of the formula (IVa) where $R_8$ is a group of the formula (V), m is zero or 1, n is a number from 1 to 10, $Y_1$ is OH, ONa, OK, a group $R_8$ or a group $-X_1Z$ or $-X_3Z$ with Z being hydrogen or methyl and $Y_2$ is hydrogen, methyl or a group

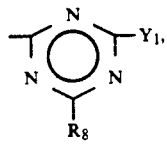

with the proviso that $X_1$ or $X_2$ or $X_3$ contains a group of the formula (II) with $R_2$ being hydrogen or methyl.

7. A composition which contains a material susceptible to degradation induced by light, heat and oxidation and a compound of the formula (I) according to claim 1.

8. A composition according to claim 7, wherein the organic material is a synthetic polymer.

9. A composition according to claim 8, which contains other conventional additives for synthetic polymers, in addition to the compounds of the formula (I).

10. A composition according to claim 7, wherein the organic material is a polyolefin.

11. A composition according to claim 7, wherein the organic material is polyethylene or polypropylene.

12. A method for stabilizing an organic material against degradation induced by light, heat and oxidation, which comprises incorporating into the organic material a compound of the formula (I) according to claim 1.

* * * * *